United States Patent [19]
Mabilat et al.

[11] Patent Number: 6,037,122
[45] Date of Patent: Mar. 14, 2000

[54] NUCLEOTIDE FRAGMENT OF THE 16S RIBOSOMAL RNA OF CORYNEBACTERIA, DERIVED PROBES AND PRIMERS, REAGENT AND METHOD OF DETECTION

[75] Inventors: Claude Mabilat, Rillieux la Pape; Raymond Ruimy, Nice, both of France

[73] Assignee: Bio Merieux, Marcy L'Etoille, France

[21] Appl. No.: 08/641,291

[22] Filed: Apr. 30, 1996

[30] Foreign Application Priority Data

May 3, 1995 [FR] France .................................. 95 05494

[51] Int. Cl.⁷ ............................. C12Q 1/68; C07H 21/02; C07H 21/04; C12N 15/00
[52] U.S. Cl. ............................ 435/6; 536/23.1; 536/24.3; 935/76; 935/77; 935/78
[58] Field of Search ................................. 536/23.1, 24.3; 435/6, 91.2

[56] References Cited

U.S. PATENT DOCUMENTS

| | | | |
|---|---|---|---|
| 5,401,631 | 3/1995 | Lane et al. .................................. | 435/6 |
| 5,620,847 | 4/1997 | Greisen et al. .............................. | 435/6 |
| 5,635,348 | 6/1997 | Leong ......................................... | 435/6 |

FOREIGN PATENT DOCUMENTS

| | | |
|---|---|---|
| 2 663 040 | 6/1990 | France . |
| 2 679 255 | 7/1991 | France . |
| 2 701 961 | 2/1993 | France . |
| WO 88/03957 | 6/1988 | WIPO . |
| WO 95/03412 | 2/1995 | WIPO . |

OTHER PUBLICATIONS

Journal of Clinical Microbiology, vol. 32, No. 2, Feb. 1992, "PCR Primers and Probes for the 16S rRNA Gene of Most Species of Pathogenic Bacteria, Including Bacteria Found in Cerebrospinal Fluid", K. Greisen et al., pp. 335–351.

Applied and Environmental Microbiology, vol. 58, No. 12, Dec. 1992, "Rapid and Sensitive Detection of Campylobacter spp. in Chicken Products by Using the Polymerase Chain Reaction", B.A.J. Giesendorf et al., pp. 3804–3808.

Microbiology, vol. 140, Oct. 1994, "In situ probing of Gram–positive bacteria with high DNA G+C content using 23S rRNA–targeted oligonucleotides", Carsten Roller et al., pp. 2849–2858.

P. Neilsen et al., "Sequence–Selective Recognition of DNA by Strand Displacement with a Thymine–Substituted Polyamide", *Science*, vol. 254, pp. 1497–1500, (1991).

Ausubel et al., *Current Protocols in Molecular Biology*, ♀4.4.3 (1987).

J. Sambrook, "Lysis of Colonies and Binding of DNA to Nitrocellulose Filters", *Molecular Cloning*, pp. 1.98–1.99 (1989).

F. Sanger et al., "DNA Sequencing with Chain–Terminating Inhibitors", *Proc. Natl. Acad. Sci. USA*, vol. 74, No. 12, pp. 5463–5467 (1977).

U. Sjorbring et al., "Polymerase Chain Reaction for Detection of Mycobacterium Tuberculosis", *Journal of Clinical Microbiology*, vol. 28, No. 10, pp. 2200–2204 (1990).

A. Dunn et al., "A Novel Method to Map Transcripts: Evidence for Homology between an Adenovirus mRNA and Discrete Multiple Regions of the Viral Gerome", *Cell*, vol. 12, pp. 23–36 (1977).

E. Southern, "Detection of Specific Sequences Among DNA Fragments Separated by Gel Electrophoresis", *J. Mol. Biol.*, vol. 98, pp. 503–517 (1975).

Giensendorf et al., Applied and Environmental Microbiology 58(12): 3804–3808 (1992).

Greisen et al., Journal of Clinical Microbiology 32(2): 335–351 (1992).

George et al., "Current Methods in Sequence Comparison and Analysis" in *Macromolecular Sequencing and Synthesis, Selected Method and Applications,* pp. 127–149 Alan R. Liss, Inc. (1988).

Pascual et al., International J. of Systematic Bacteriology 45(4): 724–728 (Oct. 1995).

*Primary Examiner*—W. Gary Jones
*Assistant Examiner*—Ethan Whisenant
*Attorney, Agent, or Firm*—Oliff & Berridge, PLC

[57] ABSTRACT

The invention relates to probes and primers derived from the 16S ribosomal RNA of pathogenic species of the genus Corynebacteria. In addition, a method of detecting and/or identifying pathogenic species of the genus Corynebacteria utilizing the probes and primers is disclosed.

24 Claims, No Drawings

```
                          SEQUENCE LISTING (1) GENERAL INFORMATION:

(iii) NUMBER OF SEQUENCES: 92

(2) INFORMATION FOR SEQ ID NO: 1:

(i) SEQUENCE CHARACTERISTICS:
             (A) LENGTH: 22 base pairs
             (B) TYPE: nucleotide
             (C) STRANDEDNESS: single
             (D) TOPOLOGY: linear (ii) MOLECULE TYPE: rRNA (xi) SEQUENCE DESCRIPTION: SEQ ID NO: 1:

ACGGAAAGGC CUAGCUUGCU AG                                              22

(2) INFORMATION FOR SEQ ID NO: 2:

(i) SEQUENCE CHARACTERISTICS:
             (A) LENGTH: 23 base pairs
             (B) TYPE: nucleotide
             (C) STRANDEDNESS: single
             (D) TOPOLOGY: linear (ii) MOLECULE TYPE: rRNA (xi) SEQUENCE DESCRIPTION: SEQ ID NO: 2:

ACGGAAAGGC AGUGCUUGCA CUG                                             23

(2) INFORMATION FOR SEQ ID NO: 3:

(i) SEQUENCE CHARACTERISTICS:
             (A) LENGTH: 22 base pairs
             (B) TYPE: nucleotide
             (C) STRANDEDNESS: single
             (D) TOPOLOGY: linear (ii) MOLECULE TYPE: rRNA (xi) SEQUENCE DESCRIPTION: SEQ ID NO: 3:

ACGGAAAGGC CAAGCUUGCU UG                                              22

(2) INFORMATION FOR SEQ ID NO: 4:
```

(i) SEQUENCE CHARACTERISTICS:
           (A) LENGTH: 24 base pairs
           (B) TYPE: nucleotide
           (C) STRANDEDNESS: single
           (D) TOPOLOGY: linear (ii) MOLECULE TYPE: rRNA (xi) SEQUENCE DESCRIPTION: SEQ ID NO: 4:

ACGGUAAGGC UCCAGCUUGC UGGG                                              24

(2) INFORMATION FOR SEQ ID NO: 5:

(i) SEQUENCE CHARACTERISTICS:
           (A) LENGTH: 24 base pairs
           (B) TYPE: nucleotide
           (C) STRANDEDNESS: single
           (D) TOPOLOGY: linear (ii) MOLECULE TYPE: rRNA (xi) SEQUENCE DESCRIPTION: SEQ ID NO: 5:

ACGGAAAGGC CUAAGCUUGC UUGG                                              24

(2) INFORMATION FOR SEQ ID NO: 6:

(i) SEQUENCE CHARACTERISTICS:
           (A) LENGTH: 24 base pairs
           (B) TYPE: nucleotide
           (C) STRANDEDNESS: single
           (D) TOPOLOGY: linear (ii) MOLECULE TYPE: rRNA (xi) SEQUENCE DESCRIPTION: SEQ ID NO: 6:

ACGGAAAGGC CCCAGCUUGC UGGG                                              24

(2) INFORMATION FOR SEQ ID NO: 7:

(i) SEQUENCE CHARACTERISTICS:
           (A) LENGTH: 24 base pairs
           (B) TYPE: nucleotide
           (C) STRANDEDNESS: single
           (D) TOPOLOGY: linear (ii) MOLECULE TYPE: rRNA (xi) SEQUENCE DESCRIPTION: SEQ ID NO: 7:

ACGGAAAGGC UCUAGCUUGC UAGG                                              24

(2) INFORMATION FOR SEQ ID NO: 8:

(i) SEQUENCE CHARACTERISTICS:
           (A) LENGTH: 26 base pairs
           (B) TYPE: nucleotide
           (C) STRANDEDNESS: single
           (D) TOPOLOGY: linear (ii) MOLECULE TYPE: rRNA (xi) SEQUENCE DESCRIPTION: SEQ ID NO: 8:

ACGGAAAGGC CCCUAGCUUG CUGGGG                                            26

(2) INFORMATION FOR SEQ ID NO: 9:

(i) SEQUENCE CHARACTERISTICS:
           (A) LENGTH: 26 base pairs
           (B) TYPE: nucleotide
           (C) STRANDEDNESS: single (D) TOPOLOGY: linear (ii) MOLECULE TYPE: rRNA (xi) SEQUENCE DESCRIPTION: SEQ ID NO: 9:

ACGGAAAGGC UCCUUGCUUG CAAGGG                                              26

(2) INFORMATION FOR SEQ ID NO: 10:

(i) SEQUENCE CHARACTERISTICS:
        (A) LENGTH: 29 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 10:

ACGGAAAGGC CCCCACUUUU UUGGUGGGG                                           29

(2) INFORMATION FOR SEQ ID NO: 11:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 11:

ACGGAAAGGC CGAAGCUUGC UUUG                                                24

(2) INFORMATION FOR SEQ ID NO: 12:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 12:

ACGGAAAGGC CUGCUUGCAG G                                                   21

(2) INFORMATION FOR SEQ ID NO: 13:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 13:

ACGGAAAGGC CUCUUCGGAG                                                     20

(2) INFORMATION FOR SEQ ID NO: 14:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 14:

ACGGAAAGGC CCCUUCGGGG                                      20

(2) INFORMATION FOR SEQ ID NO: 15:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 15:

ACGGAAAGGC UCCAGCUUGC UGGG                                 24

(2) INFORMATION FOR SEQ ID NO: 16:

(i) SEQUENCE CHARACTERISTICS:
        (A) LENGTH: 25 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 16:

ACGGAAAGGC UCCUGCUUGC UAGGG                                25

(2) INFORMATION FOR SEQ ID NO: 17:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 17:

ACGGAAAGGC AGUGCUUGCU ACUG                                 24

(2) INFORMATION FOR SEQ ID NO: 18:

(i) SEQUENCE CHARACTERISTICS:
        (A) LENGTH: 25 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 18:

ACGGAAAGGC CGCAGCUUGC UGCGG                                25

(2) INFORMATION FOR SEQ ID NO: 19:

(i) SEQUENCE CHARACTERISTICS:
        (A) LENGTH: 19 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 19:

ACGGAAAGGC CCCUUCGGG                                       19

(2) INFORMATION FOR SEQ ID NO: 20:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 20:

ACGGAAAGGC CCCUGCUUGC AGG                                         23

(2) INFORMATION FOR SEQ ID NO: 21:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 21:

CAUGCUUUAG UGUGUGUG                                                 18

(2) INFORMATION FOR SEQ ID NO: 22:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 22:

CACAUUUUGG AUGGUGUG                                                 18

(2) INFORMATION FOR SEQ ID NO: 23:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 23:

CAUGGUGUGG AUGCUGUG                                                 18

(2) INFORMATION FOR SEQ ID NO: 24:

(i) SEQUENCE CHARACTERISTICS:
        (A) LENGTH: 19 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 24:

CAUCCUUUAG UGUGUGAUG                                              19

(2) INFORMATION FOR SEQ ID NO: 25:

(i) SEQUENCE CHARACTERISTICS:

(A) LENGTH: 17 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 25:

CGCACCGUGA GGGUGUG                                                17

(2) INFORMATION FOR SEQ ID NO: 26:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 26:

CGUGCUUUAG UGUGUGCG                                               18

(2) INFORMATION FOR SEQ ID NO: 27:

(i) SEQUENCE CHARACTERISTICS:
        (A) LENGTH: 17 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 27:

GUAUCUUUUG UGGGUGU                                                17

(2) INFORMATION FOR SEQ ID NO: 28:

(i) SEQUENCE CHARACTERISTICS:
        (A) LENGTH: 17 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 28:

GGUCUUUGGU GUGAUUG                                                17

(2) INFORMATION FOR SEQ ID NO: 29:

(i) SEQUENCE CHARACTERISTICS:
        (A) LENGTH: 19 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 29:

CAUGGUUUAG UGUCUCAUG                                              19

(2) INFORMATION FOR SEQ ID NO: 30:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 30:

CCGUCUUUAG UGUGGUGG                                                      18

(2) INFORMATION FOR SEQ ID NO: 31:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 31:

CUGCAUGUUG GUGUGUGG                                                      18

(2) INFORMATION FOR SEQ ID NO: 32:

(i) SEQUENCE CHARACTERISTICS:
        (A) LENGTH: 7 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 32:

CUUUGUG                                                                   7

(2) INFORMATION FOR SEQ ID NO: 33:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 33:

CGCGCUUUAG UGUGUGUG                                                      18

(2) INFORMATION FOR SEQ ID NO: 34:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 34:

CGCAUCGUGG UUGGUGUG                                                      18

(2) INFORMATION FOR SEQ ID NO: 35:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 35:

```
AACUUUUUGG AUAUUGUU                                              18

(2) INFORMATION FOR SEQ ID NO: 36:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 36:

AGCUGUUUAG UGUCAGUU                                              18

(2) INFORMATION FOR SEQ ID NO: 37:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 37:

CAAUCUUUAG UGUGGUUG                                              18

(2) INFORMATION FOR SEQ ID NO: 38:

(i) SEQUENCE CHARACTERISTICS:
        (A) LENGTH: 17 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 38:

GAAGCUUUUG UGACGGU                                               17

(2) INFORMATION FOR SEQ ID NO: 39:

(i) SEQUENCE CHARACTERISTICS:
        (A) LENGTH: 19 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 39:

GAAGCGUAUU UGUGACGGU                                             19

(2) INFORMATION FOR SEQ ID NO: 40:

(i) SEQUENCE CHARACTERISTICS:
        (A) LENGTH: 17 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 40:

GAAGGGUUUC UGACGGU                                               17
```

(2) INFORMATION FOR SEQ ID NO: 41:

(i) SEQUENCE CHARACTERISTICS:
        (A) LENGTH: 17 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 41:

GAAGCGUGUG UGACGGU                                              17

(2) INFORMATION FOR SEQ ID NO: 42:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 42:

GAAGCCUUUN NNAAGGUGAC GGU                                       23

(2) INFORMATION FOR SEQ ID NO: 43:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 43:

GAAGCACUGU GUGGUGACGG U                                         21

(2) INFORMATION FOR SEQ ID NO: 44:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 44:

GAAGCGUUUU GUGACGGU                                             18

(2) INFORMATION FOR SEQ ID NO: 45:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 45:

GAAGCUUUUU GUGACGGU                                             18

(2) INFORMATION FOR SEQ ID NO: 46:

(i) SEQUENCE CHARACTERISTICS:
        (A) LENGTH: 18 base pairs (B) TYPE: nucleotide
         (C) STRANDEDNESS: single
         (D) TOPOLOGY: linear (ii) MOLECULE TYPE: rRNA (xi) SEQUENCE DESCRIPTION: SEQ ID NO: 46:

GAAGCAUUAU GUGACGGU                                                    18

(2) INFORMATION FOR SEQ ID NO: 47:

(i) SEQUENCE CHARACTERISTICS:
         (A) LENGTH: 17 base pairs
         (B) TYPE: nucleotide
         (C) STRANDEDNESS: single
         (D) TOPOLOGY: linear (ii) MOLECULE TYPE: rRNA (xi) SEQUENCE DESCRIPTION: SEQ ID NO: 47:

GAAGCGUAAG UGACGGU                                                     17

(2) INFORMATION FOR SEQ ID NO: 48:

(i) SEQUENCE CHARACTERISTICS:
         (A) LENGTH: 19 base pairs
         (B) TYPE: nucleotide
         (C) STRANDEDNESS: single
         (D) TOPOLOGY: linear (ii) MOLECULE TYPE: rRNA (xi) SEQUENCE DESCRIPTION: SEQ ID NO: 48:

GAAGCCUUCG GGUGACGGU                                                   19

(2) INFORMATION FOR SEQ ID NO: 49:

(i) SEQUENCE CHARACTERISTICS:
         (A) LENGTH: 24 base pairs
         (B) TYPE: nucleotide
         (C) STRANDEDNESS: single
         (D) TOPOLOGY: linear (ii) MOLECULE TYPE: rRNA (xi) SEQUENCE DESCRIPTION: SEQ ID NO: 49:

CGUCUGUGAA AUUCCGGGGC UUAA                                             24

(2) INFORMATION FOR SEQ ID NO: 50:

(i) SEQUENCE CHARACTERISTICS:
         (A) LENGTH: 24 base pairs
         (B) TYPE: nucleotide
         (C) STRANDEDNESS: single
         (D) TOPOLOGY: linear (ii) MOLECULE TYPE: rRNA (xi) SEQUENCE DESCRIPTION: SEQ ID NO: 50:

CGUUUGUGUA AGCNNNCAGC UUAA                                             24

(2) INFORMATION FOR SEQ ID NO: 51:

(i) SEQUENCE CHARACTERISTICS:
         (A) LENGTH: 24 base pairs
         (B) TYPE: nucleotide
         (C) STRANDEDNESS: single
         (D) TOPOLOGY: linear (ii) MOLECULE TYPE: rRNA (xi) SEQUENCE DESCRIPTION: SEQ ID NO: 51:

CGUCUGUGAA AUCCCGGGGC UUAA                                                 24

(2) INFORMATION FOR SEQ ID NO: 52:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 52:

CGUCUGUGGA AGUCCGGGGC UUAA                                                 24

(2) INFORMATION FOR SEQ ID NO: 53:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 53:

CGUUUGUGUA AGUCCACGGC UUAA                                                 24

(2) INFORMATION FOR SEQ ID NO: 54:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 54:

CGUCUGUGAA AUUCCACAGC UUAA                                                 24

(2) INFORMATION FOR SEQ ID NO: 55:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 55:

CGUCUGUGUA AUCCAGGGGC UUAA                                                 24

(2) INFORMATION FOR SEQ ID NO: 56:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 56:

CGUUUGUGUA AGUCCACAGC UUAA                                                                    24

(2) INFORMATION FOR SEQ ID NO: 57:

(i) SEQUENCE CHARACTERISTICS:
        (A) LENGTH: 15 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 57:

UAGGUGUGAG GGUCU                                                                              15

(2) INFORMATION FOR SEQ ID NO: 58:

(i) SEQUENCE CHARACTERISTICS:
        (A) LENGTH: 15 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 58:

UAGGUGUGAG UCCCU                                                                              15

(2) INFORMATION FOR SEQ ID NO: 59:

(i) SEQUENCE CHARACTERISTICS:
        (A) LENGTH: 15 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 59:

UAGGUGUAGG GGGCU                                                                              15

(2) INFORMATION FOR SEQ ID NO: 60:

(i) SEQUENCE CHARACTERISTICS:
        (A) LENGTH: 16 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 60:

UAGGUGUGGG UUUCCU                                                                             16

(2) INFORMATION FOR SEQ ID NO: 61:

(i) SEQUENCE CHARACTERISTICS:
        (A) LENGTH: 15 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 61:

UAGGUGUAGG GGACU                                                                              15

(2) INFORMATION FOR SEQ ID NO: 62:

(i) SEQUENCE CHARACTERISTICS:
        (A) LENGTH: 15 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 62:

UAGGUGUGGG GAUCU                                                        15

(2) INFORMATION FOR SEQ ID NO: 63:

(i) SEQUENCE CHARACTERISTICS:
        (A) LENGTH: 15 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 63:

UAGGUGUGAG AUCCU                                                        15

(2) INFORMATION FOR SEQ ID NO: 64:

(i) SEQUENCE CHARACTERISTICS:
        (A) LENGTH: 16 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 64:

UAGGUGUGGG GGUUUN                                                       16

(2) INFORMATION FOR SEQ ID NO: 65:

(i) SEQUENCE CHARACTERISTICS:
        (A) LENGTH: 14 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 65:

UAGGUGUGGG GACC                                                         14

(2) INFORMATION FOR SEQ ID NO: 66:

(i) SEQUENCE CHARACTERISTICS:
        (A) LENGTH: 15 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 66:

UAGGUGUAGG GACCU                                                        15

(2) INFORMATION FOR SEQ ID NO: 67:

(i) SEQUENCE CHARACTERISTICS:
        (A) LENGTH: 16 base pairs
        (B) TYPE: nucleotide

```
        (C) STRANDEDNESS: single
        (D) TOPOLOGY: linear (ii) MOLECULE TYPE: rRNA (xi) SEQUENCE DESCRIPTION: SEQ ID NO: 67:

UAGGUGUGAG UCCCNU                                                          16

(2) INFORMATION FOR SEQ ID NO: 68:

(i) SEQUENCE CHARACTERISTICS:
        (A) LENGTH: 15 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 68:

UAGGUGUGGG GAUUU                                                           15

(2) INFORMATION FOR SEQ ID NO: 69:

(i) SEQUENCE CHARACTERISTICS:
        (A) LENGTH: 16 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 69:

GACUUUCGUG CCGUAG                                                          16

(2) INFORMATION FOR SEQ ID NO: 70:

(i) SEQUENCE CHARACTERISTICS:
        (A) LENGTH: 16 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 70:

GGGGUUCGUG CCGUAG                                                          16

(2) INFORMATION FOR SEQ ID NO: 71:

(i) SEQUENCE CHARACTERISTICS:
        (A) LENGTH: 16 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 71:

GUCUUCUGUG CCGUAG                                                          16

(2) INFORMATION FOR SEQ ID NO: 72:

(i) SEQUENCE CHARACTERISTICS:
        (A) LENGTH: 16 base pairs
        (B) TYPE: nucleotide
        (C) STRANDEDNESS: single
        (D) TOPOLOGY: linear (ii) MOLECULE TYPE: rRNA
```

(xi) SEQUENCE DESCRIPTION: SEQ ID NO: 72:

GAUUUCCGUG CCGUAG                                                           16

(2) INFORMATION FOR SEQ ID NO: 73:

(i) SEQUENCE CHARACTERISTICS:
                (A) LENGTH: 16 base pairs
                (B) TYPE: nucleotide
                (C) STRANDEDNESS: single
                (D) TOPOLOGY: linear (ii) MOLECULE TYPE: rRNA (xi) SEQUENCE DESCRIPTION: SEQ ID NO: 73:

GGGUUUUGUG CCGUAG                                                           16

(2) INFORMATION FOR SEQ ID NO: 74:

(i) SEQUENCE CHARACTERISTICS:
                (A) LENGTH: 16 base pairs
                (B) TYPE: nucleotide
                (C) STRANDEDNESS: single
                (D) TOPOLOGY: linear (ii) MOLECULE TYPE: rRNA (xi) SEQUENCE DESCRIPTION: SEQ ID NO: 74:

GAUUCCCGUG CCGUAG                                                           16

(2) INFORMATION FOR SEQ ID NO: 75:

(i) SEQUENCE CHARACTERISTICS:
                (A) LENGTH: 16 base pairs
                (B) TYPE: nucleotide
                (C) STRANDEDNESS: single
                (D) TOPOLOGY: linear (ii) MOLECULE TYPE: rRNA (xi) SEQUENCE DESCRIPTION: SEQ ID NO: 75:

GGUUUCNGUG CCGUAG                                                           16

(2) INFORMATION FOR SEQ ID NO: 76:

(i) SEQUENCE CHARACTERISTICS:
                (A) LENGTH: 16 base pairs
                (B) TYPE: nucleotide
                (C) STRANDEDNESS: single
                (D) TOPOLOGY: linear (ii) MOLECULE TYPE: rRNA (xi) SEQUENCE DESCRIPTION: SEQ ID NO: 76:

GUUUUCUGUG CCGUAG                                                           16

(2) INFORMATION FOR SEQ ID NO: 77:

(i) SEQUENCE CHARACTERISTICS:
                (A) LENGTH: 16 base pairs
                (B) TYPE: nucleotide
                (C) STRANDEDNESS: single
                (D) TOPOLOGY: linear (ii) MOLECULE TYPE: rRNA (xi) SEQUENCE DESCRIPTION: SEQ ID NO: 77:

GGUUUCUGUG CCGUAG                                                           16

(2) INFORMATION FOR SEQ ID NO: 78:

(i) SEQUENCE CHARACTERISTICS:
        (A) LENGTH: 16 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 78:

GGGGUUUGUG CCGUAG                                                 16

(2) INFORMATION FOR SEQ ID NO: 79:

(i) SEQUENCE CHARACTERISTICS:
        (A) LENGTH: 16 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 79:

GGGAUUUGUG CCGUAG                                                 16

(2) INFORMATION FOR SEQ ID NO: 80:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 80:

UGCAGGAUCG GCGUAGUGAU                                        20

(2) INFORMATION FOR SEQ ID NO: 81:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 81:

CACCAGAUCG CCGUAGAGAU                                        20

(2) INFORMATION FOR SEQ ID NO: 82:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 82:

UACAGGAUCG CGCCAGAGAU                                        20

(2) INFORMATION FOR SEQ ID NO: 83:

```
    (i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 83:

UACAGGAUCG CUGCAGAGAU                                              20

(2) INFORMATION FOR SEQ ID NO: 84:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 84:

GGCAGGACCG GCGUGGAGAC                                              20

(2) INFORMATION FOR SEQ ID NO: 85:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 85:

CACUGGAUUG CCAUGGAGAC                                              20

(2) INFORMATION FOR SEQ ID NO: 86:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 86:

UGCAGGAUUG GGUCAGAGAU                                              20

(2) INFORMATION FOR SEQ ID NO: 87:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 87:

CACCAGACGG UCGUAGAGAU A                                            21

(2) INFORMATION FOR SEQ ID NO: 88:

(i) SEQUENCE CHARACTERISTICS:
        (A) LENGTH: 20 base pairs
        (B) TYPE: nucleotide
        (C) STRANDEDNESS: single
```

(D) TOPOLOGY: linear (ii) MOLECULE TYPE: rRNA (xi) SEQUENCE DESCRIPTION: SEQ ID NO: 88:

CACUAGAUCG CUGUAGAGAU                                                  20

(2) INFORMATION FOR SEQ ID NO: 89:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 89:

CACCGGAUCG GGCUAGAGAU                                                  20

(2) INFORMATION FOR SEQ ID NO: 90:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 90:

UACGGGAUCG CCGCAGAGAU                                                  20

(2) INFORMATION FOR SEQ ID NO: 91:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 91:

UACAAGACAG GCGUAGAGAU                                                  20

(2) INFORMATION FOR SEQ ID NO: 92:

(i) SEQUENCE CHARACTERISTICS:
        (A) LENGTH: 1475 base pairs
        (B) TYPE: nucleotide
        (C) STRANDEDNESS: single
        (D) TOPOLOGY: linear (ii) MOLECULE TYPE: rRNA (xi) SEQUENCE DESCRIPTION: SEQ ID NO: 92:

CGCUGGCGGC GUGCUUAACA CAUGCAAGUC GAACGGAAAG GCCUAGCUUG CUAGGUACUC       60

GAGUGGCGAA CGGGUGAGUA ACACGUGGGU GAUCUGCCUC GUACUUCGGG AUAAGCCUGG      120

GAAACUGGGU CUAAUACUGG AUAGGACCAU GCUUUAGUGU GUGUGGUGGA AAGUUUUUCG      180

GUACGAGAUG AGCCCGCGGC CUAUCAGCUU GUUGGUGGGG UAAUGGCCUA CCAAGGCGUC      240

GACGGGUAGC CGGCCUGAGA GGGUGGACGG CCACAUUGGG ACUGAGAUAC GGCCCAGACU      300

CCUACGGGAG GCAGCAGUGG GGAAUAUUGC ACAAUGGGCG CAAGCCUGAU GCAGCGACGC      360

CGCGUGGGGG AUGACGGCCU UCGGGUUGUA AACCUCUUUC GCUAGGGACG AAGCUUUUGU      420

-continued

```
GACGGUACCU AGAUAAGAAG CACCGGCUAA CUACGUGCCA GCAGCCGCGG UAAUACGUAG      480

GGUGCGAGCG UUGUCCGGAA UUACUGGGCG UAAAGAGCUC GUAGGUGGUU UGUCGCGUCG      540

UCUGUGAAAU UCCGGGGCUU AACUUCGGGC GUGCAGGCGA UACGGGCAUA ACUUGAGUGC      600

UGUAGGGGAG ACUGGAAUUC CUGGUGUAGC GGUGGAAUGC GCAGAUAUCA GGAGGAACAC      660

CGAUGGCGAA GGCAGGUCUC UGGGCAGUAA CUGACGCUGA GGAGCGAAAG CAUGGGGAGC      720

GAACAGGAUU AGAUACCCUG GUAGUCCAUG CCGUAAACGG UGGGCGCUAG GUGUGAGGGU      780

CUUCCACGAC UUUCGUGCCG UAGCUAACGC AUUAAGCGCC CCGCCUGGGG AGUACGGCCG      840

CAAGGCUAAA ACUCAAAGGA AUUGACGGGG GCCCGCACAA GCGGCGGAGC AUGUGGAUUA      900

AUUCGAUGCA ACGCGAAGAA CCUUACCUGG GCUUGACAUA UGCAGGAUCG GCGUAGUGAU      960

ACGUUUUCCC UUGUGGUCUG UAUACAGGUG GUGCAUGGUU GUCGUCAGCU CGUGUCGUGA     1020

GAUGUUGGGU UAAGUCCCGC AACGAGCGCA ACCCUUGUCU UAUGUUGCCA GCACGUGAUG     1080

GUGGGGACUC AUGAGAGACU GCCGGGGUUA ACUCGGAGGA AGGUGGGGAU GACGUCAAAU     1140

CAUCAUGCCC CUUAUGUCCA GGGCUUCACA CAUGCUACAA UGGUCGGUAC AACGCGCUGC     1200

GAGCCUGUGA GGGUGAGCGA AUCGCUGAAA GCCGGCCUCA GUUCGGAUUG GGGUCUGCAA     1260

CUCGACCCCA UGAAGUCGGA GUCGCUAGUA AUCGCAGAUC AGCAACGCUG CGGUGAAUAC     1320

GUNCCCGGGC CUUGUACACA CCGCCCGUCA CGUCAUGAAA GUUGGUAACA CCCGAAGCCA     1380

GUGGCCUAAC CCUUGUGGGG GGGAGCUGUC GAAGGUGGNA UCGGCGAUUG GNACGAAGUC     1440

GUAACAAGGU AGCCGUACCG GAAGGUGCGG GCUGG                                1475
```

NUCLEOTIDE FRAGMENT OF THE 16S RIBOSOMAL RNA OF CORYNEBACTERIA, DERIVED PROBES AND PRIMERS, REAGENT AND METHOD OF DETECTION

The present belongs to the field of the techniques of detection and/or amplification of nucleic acid material using oligonucleotide probes or primers, and to their application,

SUMMARY OF THE INVENTION

The present invention remedies the drawbacks mentioned above for revealing the presence of bacteria of the genus Corynebacterium, and more especially of the pathogenic species, by the use of a genetic marker in a method of detection by hybridization of nucleic acids combining specificity, sensitivity and speed.

TABLE

|  | endocarditis | septicemia | urinary infections | pneumonia | wound infections (suppuration, abscesses) | pharyngitis | adenophathy |
|---|---|---|---|---|---|---|---|
| *Corynebacterium jelkeium* | +++ | ++ |  |  | + |  |  |
| *Corynebacterium minutissimum* |  | + |  |  |  |  |  |
| *Corynebacterium pseudotuberculosis* |  |  |  | + |  |  | + |
| *Corynebacterium ulcerans* |  |  |  |  |  | + |  |
| *Corynebacterium xerosis* | + | + |  |  | + |  |  |
| Corynebacterium du groupe A4 |  | + |  |  |  |  |  |
| Corynebacterium du groupe D2 |  |  | +++ |  | + |  |  |
| Corynebacterium du groupe G2 | + | + |  |  |  |  |  |
| Corynebacterium du groupe I |  |  |  |  | + |  |  |
| *Arcanobacterium haemolyticum* |  |  |  |  | + | + |  |
| *Rhodococcus equl* |  |  |  | + |  |  |  | in particular, in testing for the presence or in the identification of bacteria of the genus Corynebacterium.

BACKGROUND OF THE INVENTION

Corynebacteria are commensal bacteria constituting a group which is heterogeneous from the morphological, taxonomic, pathogenic and therapeutic standpoints. This heterogeneity was, for a long time, responsible for a lack of knowledge of this group and limited the identification of the different strains. In man, the pathogenicity of the species belonging to the genus Corynebacterium is very variable, and many corynebacteria form part of the normal flora of the skin and the mucosae. Thus, from a pathological standpoint, some strains are highly pathogenic for man (*Corynebacterium diphtheriae*), but most are opportunistic bacteria responsible for infections in immunosuppressed or weakened patients. In effect, from an epidemiological point of view, the pathogenic power of corynebacteria was for a long time limited to diphtheria (*Corynebacterium diphtheriae*), but this disease is currently on the decline on account, in particular, of obligatory vaccination measures, and has given way to new pathologies associated with the advances in hospital medicine. Thus, corynebacteria are more and more frequently isolated in the context of nosocomial infections.

Since these infections caused by corynebacteria (see table below) occur essentially in greatly weakened patients, it is important to have at one's disposal a bacteriological diagnostic test which is sufficiently specific and sensitive to permit a rapid and selective detection of the species responsible, so as to implement a suitable therapy as quickly as possible. Now, at the resent time, analytical laboratories have at their disposal only biochemical and bacteriological tests limited by steps of isolation and of bacterial culture which are essential to the tests, and which are often not sufficiently specific and sensitive to diagnose the presence of a particular species of corynebacteria, and more especially of a pathogenic species, in a biological sample.

Before the invention is described, different terms used in the description and the claims will now be defined:

pathogenic species belonging to the genus Corynebacterium is understood to mean the species capable of causing, in man or in animals, an infection or a secondary infection, as opposed to the species of the same genus which make up the normal flora of the skin and the mucosae; any species which does not induce a pathological state in a patient such as a healthy patient but causes lesions in another patient such as an immunosuppressed patient is also considered to be a pathogenic species; in particular, some species which are non- pathogenic in healthy subjects are encountered in the hospital environment where immunosuppressed patients, in whom these same species are pathogenic, are staying;

"nucleic acid extracted from bacteria" is understood to mean either the total nucleic acid, or the ribosomal RNA, especially the 16S rRNA, or the genomic DNA, or alternatively the DNA obtained from the reverse transcription of the ribosomal RNA, especially the 16S RNA;

according to the invention, a nucleotide fragment or an oligonucleotide is a linked arrangement of monomers, characterized by the informational sequence of the natural nucleic acids, capable of hybridizing with a nucleotide fragment under predetermined conditions, it being possible for the linked arrangement to contain monomers of different structures and to be obtained from a natural nucleic acid molecule and/or by genetic recombination and/or by chemical synthesis;

thus, a monomer can be a natural nucleotide of nucleic acid whose constituent components are sugar, a phosphate group and a nitrogenous base; in RNA the sugar is ribose, in DNA the sugar is 2-deoxyribose; depending on whether the nucleic acid is DNA or RNA, the nitrogenous base is chosen from adenine, guanine, uracil, cytosine and thymine; or a nucleotide modified in at least one of the three constituent components; as an example, the modification can occur in the bases, generating modified bases such as inosine, 5-methyldeoxycytidine, deoxyuridine, 5-(dimethylamino)deoxyuridine, 2,6-diaminopurine, 5-bromodeoxyuridine and any other modified base favoring hybridization, in the sugar, namely the replacement of at least one deoxyribose by a polyamide (P. E. Nielsen et al., Science, 254, 1497–1500 (1991)), or in the phosphate group, for example its replacement by esters chosen, in particular, from diphosphate, alkyl- and arylphosphonate and phosphorothioate esters;

"informational sequence", is understood to mean any ordered succession of monomers whose chemical nature and order in a reference direction constitute an item of information of the same quality as that of the natural nucleic acids;

"hybridization" is understood to mean the process during which, under suitable conditions, two nucleotide fragments having sufficiently complementary sequences are capable of associating via stable and specific hydrogen bonds to form a double strand. The hybridization conditions are determined by the "stringency", that is to say the severity of the working conditions; hybridization is all the more specific for being performed at higher stringency; the stringency is a function, in particular, of the base composition of the probe/target duplex, as well as of the degree of mismatch between two nucleic acids; the stringency may also be a function of the parameters of the hybridization reaction, such as the concentration and type of ionic species present in the hybridization solution, the nature and concentration of denaturating agents and/or the hybridization temperature; the stringency of the conditions under which a hybridization should be carried out depends, in particular, on the probes used; all these data are well known to a person skilled in the art, and the appropriate conditions may be determined, where appropriate, in each case by routine experiments; in general, depending on the length of the probes used, the temperature for the hybridization reaction is between approximately 20 and 65° C., and especially between 35 and 65° C., in a saline solution at a concentration of approximately 0.8 to 1M;

a probe is a nucleotide fragment comprising at least 5 monomers, and advantageously at least 8 monomers, possessing a specificity of hybridization under particular conditions to form a hybridization complex with a nucleotide fragment having a particular nucleotide sequence included in the ribosomal RNA, or the DNA obtained by reverse transcription of said ribosomal RNA, or the DNA of which said ribosomal RNA is the transcription product; a probe may be used for diagnostic purposes and be, in this case, a capture and/or detection probe, or for therapeutic purposes;

the capture probe may be immobilized on a solid support by any suitable means, that is to say directly or indirectly, for example by covalent bonding or passive adsorption;

the detection probe is labeled by means of a label chosen from radioactive isotopes, enzymes chosen, in particular, from peroxidase and alkaline phosphatase and those capable of hydrolyzing a chromogenic, fluorogenic or luminescent substrate, chromophoric chemical compounds, chromogenic, fluorogenic or luminescent compounds, nucleotide base analogs and biotin;

the probes used for diagnostic purposes of the invention may be employed in all known hybridization techniques, and in particular the techniques termed "dot-blot" (Maniatis et al., Molecular Cloning, Cold Spring Harbor, 1982), "Southern blot" (Southern E. M., J. Mol. Biol., 98, 503 (1975)), "northern blot", which is a technique identical to the "Southern blot" technique but which uses RNA as target, and the sandwich technique (Dunn A. R., Hassel J. A., Cell, 12, 23 (1977)); advantageously, the sandwich technique is used in the present invention, comprising a specific capture probe and/or a specific detection probe, on the understanding that the capture probe and the detection probe must possess an at least partially different nucleotide sequence;

another application of the invention is a therapeutic probe for treating infections due to corynebacteria, said probe being capable of hybridizing in vivo with the 16S ribosomal RNA of said bacteria and/or with the genomic DNA, to block the phenomena of translation and/or transcription;

a primer is a probe comprising from 5 to 30 monomers, possessing a specificity of hybridization under particular conditions for the initiation of an enzymatic polymerization, for example in an amplification technique such as PCR (polymerase chain reaction), in an elongation process such as sequencing, in a method of reverse transcription or the like;

homology characterizes the degree of identity of two nucleotide fragments compared: it is measured by the percentage identity which is determined, in particular, by direct comparison of nucleotide sequences with respect to reference nucleotide sequences;

any nucleotide fragment is termed equivalent to or derived from a reference fragment if it possesses a nucleotide sequence equivalent to the reference sequence, such as:
a) any fragment capable of hybridizing at least partially with the complement of the reference fragment,
b) any fragment whose alignment with the reference fragment leads to the revelation of a larger number of identical contiguous bases than with any other fragment originating from another taxonomic group,
c) any fragment resulting or capable of resulting from the natural variability of the species from which it is obtained,
d) any fragment capable of resulting from genetic engineering techniques applied to the reference fragment,
e) any fragment differing from the reference fragment by insertion, deletion or substitution of at least one monomer, or extension or shortening at one of its ends at least.

In particular, the probes and primers according to the present invention are those whose sequences are identical or equivalent to one of the sequences identified below, in particular the sequences possessing at least 70% homology with one of said sequences and a succession of at least 5 contiguous monomers belonging to this sequence.

According to the invention, single-stranded nucleotide fragments of the 16S ribosomal RNA belonging to specific regions of at least one species of corynebacteria have been determined. For 21 pathogenic species of corynebacteria, these fragments are shown in the sequence listing given at the end of the description, and identified by their number SEQ ID NO 1 to 91. These 21 pathogenic species are the following:

*Corynebacterium afermantans afermantans*
*Corynebacterium afermantans lipophilum*
*Corynebacterium amycolatum*
*Corynebacterium argentoratense*
*Corynebacterium asperum*
*Corynebacterium bovis*
*Corynebacterium cystitidis*
*Corynebacterium diphtheriae*
*Corynebacterium flavescens*
*Corynebacterium jeikeium*
*Corynebacterium matruchotii*
*Corynebacterium minutissimum*
*Corynebacterium mycetoides*
*Corynebacterium pilosum*
*Corynebacterium pseudodiphteriticum*
*Corynebacterium pseudotuberculosis*
*Corynebacterium seminale*
*Corynebacterium sp group F-1*
*Corynebacterium striatum*
*Corynebacterium ulcerans*
*Corynebacterium urealyticum*

The fragments of the invention are defined by a numbering of the nucleotides using as reference the numbering of the nucleotide sequence of the 16S ribosomal RNA of *Corynebacterium diphtheriae*, which has been completely identified by the Applicant and is described at the end of the description under the reference SEQ ID NO 92.

The single-stranded nucleotide fragments of the invention possess a nucleotide sequence chosen from the following sequences (numbering with reference to SEQ ID NO 92):

beginning at nucleotide No. 39 and ending at nucleotide No. 67
beginning at nucleotide No. 162 and ending at nucleotide No. 182
beginning at nucleotide No. 433 and ending at nucleotide No. 461
beginning at nucleotide No. 575 and ending at nucleotide No. 598
beginning at nucleotide No. 805 and ending at nucleotide No. 820
beginning at nucleotide No. 826 and ending at nucleotide No. 842
beginning at nucleotide No. 980 and ending at nucleotide No. 1000 of the 16S subunit of the ribosomal RNA of any pathogenic species belonging to the genus Corynebacterium, according to the sequencing of said subunit of *Corynebacterium diphtheriae*, and their complementary sequences.

More especially, the nucleotide sequences of the fragments of the invention are chosen from the sequences SEQ ID NO 1 to SEQ ID NO 91 described at the end of the description, and their complementary sequences.

According to the above definition, the fragments of the invention are RNA fragments, but they can also be single-stranded DNA fragments resulting from the reverse transcription of the abovementioned RNA fragments, or their complementary fragments, as well as single-stranded fragments of genomic DNA whose transcription products are the abovementioned RNA fragments, or their complementary fragments.

Another subject according to the present invention is nucleic acid probes or primers specific for pathogenic species of corynebacteria.

Preferred probes are those possessing a sequence included in the sequences (numbering with reference to SEQ ID NO 92):

beginning at nucleotide No. 39 and ending at nucleotide No. 67
beginning at nucleotide No. 162 and ending at nucleotide No. 182
beginning at nucleotide No. 433 and ending at nucleotide No. 461
beginning at nucleotide No. 575 and ending at nucleotide No. 598
beginning at nucleotide No. 805 and ending at nucleotide No. 820
beginning at nucleotide No. 826 and ending at nucleotide No. 842
beginning at nucleotide No. 980 and ending at nucleotide No. 1000, and their complementary sequences, and more especially a sequence included in the identified sequences SEQ ID NO 1 to SEQ ID NO 91 and their complementary sequences.

Another subject of the invention is a primer for the specific reverse transcription of the 16S ribosomal RNA sequence of corynebacteria into a complementary DNA sequence, or a primer, in particular, for the specific amplification by a polymerization chain reaction of the DNA sequence complementary to a 16S ribosomal RNA sequence of pathogenic corynebacteria.

The value of the probes and primers of the invention was, in addition, demonstrated when it was observed that they are specific for the pathogenic species of corynebacteria compared with species belonging to a different genus of Corynebacterium but phylogenetically close to corynebacteria.

The invention also relates to a reagent for detecting and/or identifying at least one pathogenic species of corynebacteria in a biological sample, comprising at least one probe of the invention, and especially a capture probe and a detection probe, either or both of these corresponding to the definition of a probe according to the invention. The reagent can comprise a mixture of probes of the invention with the object of detecting at least two pathogenic species of corynebacteria.

Lastly, the invention provides a method for detecting selectively and/or identifying a pathogenic species of corynebacteria in a biological sample, according to which the 16S ribosomal RNA extracted from the bacteria present in the sample, and denatured where appropriate, or the extracted and denatured genomic DNA of the bacteria, or the DNA obtained from the reverse transcription of the 16S ribosomal RNA, is exposed to at least one probe of the invention, and the hybridization of said probe is detected.

Preferably, before the DNA is exposed to the probe of the invention, an amplification of this DNA is carried out in the presence of an appropriate enzyme system and at least one amplification primer of the invention, and optionally a eubacterial primer.

The subjects of the invention and some of their applications are described below in Examples 1 and 2.

EXAMPLE 1

Revelation of the specificity of the probes and primers of the invention with respect to 22 phylogenetically close species of corynebacteria.

For 22 species not belonging to the genus Corynebacterium, fragments of the 16S ribosomal RNA corresponding to the fragments of the invention were determined.

The species are the following: *D. maris*, D. sp @1, D. sp. @2, D. sp @3, *G. aichiensis*, *G. bronchialis* @1, *G. sputi*

@1, *G. terrae* @1, *M. tuberculosis* @2, *N. asteroides* @1, *N. brasiliensis, N. carnea, N. nova, N. seriolae*, N. sp @1, *R. equi* @1, *R. erythropolis* @1, *R. fascians* @1, *R. globerulus* @1, *R. luteus, R. rhodochrous* @1, *T. paurometabolum* @1.

These fragments were determined from the complete sequencing of the 16S ribosomal RNA of these species.

The total nucleic acid of the strains used was isolated by the method of Sjö bring et al. (1990. Polymerase chain reaction for detection of *Mycobacterium tuberculosis*. J. Clin. Microbiol. 28(10):2200–2204). PCR amplification products which cover 90% of the sequence were generated from the ribosomal RNA using amplification primers of eubacterial specificity.

The amplification products obtained were sequenced directly by the chain termination method (Sanger et al., Proc. Natl. Acad. Sci. U.S.A., 1977, 74: 5463–5467), by thermal cyclization using a heat-stable Taq DNA polymerase (Perkin).

An alignment of the fragments obtained with the fragments thus determined reveals the specific character of the fragments of the invention.

EXAMPLE 2

Use of a specific probe directed against the 16S ribosomal RNA for the identification of *Corynebacterium striatum*.

The specificity of the probe corresponding to the complementary strand of the fragment beginning at nucleotide No. 6 and ending at nucleotide No. 22 of SEQ NO 18 was tested for the strains of *Corynebacterium striatum*.

A collection of strains of corynebacteria was tested by hybridization with the 16S ribosomal RNA and enabled the specificity of this probe to be established a posteriori.

The hybridization of the ribosomal RNAs of a target bacterium was conducted according to the nonradioactive and semi-automated detection method described in French Patent No 90/07249. A capture probe S8L corresponding to a probe of eubacterial specificity (described in Patent Application FR No. 93/02127) and an oligonucleotide (corresponding to the probe defined at the beginning of Example 2) -enzyme specific detection conjugate are used. The manipulation was conducted in a microtitration plate according to the following protocol.

The ribosomal RNA of the strains was extracted according to the basic protocol for extraction of the RNA of Gram-positive bacteria described in "Current Protocols in Molecular Biology" 1987, Ausubel FM et al., Wiley interscience, New York. A solution of 1 ng/µl of the capture oligonucleotide, the 5' end of which has reacted with the reagent Aminolink 2 (an amine having the following structure:

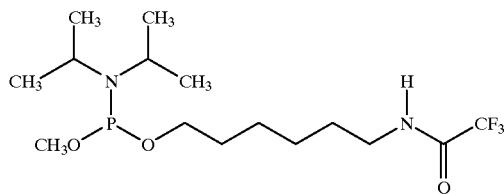

(Applied Biosystems, Foster City, Calif.), in PBX 3 (0.45 M NaCl, 0.15 M sodium phosphate, pH 7.0) is introduced into a microtitration plate (Nunc 439454). The plate is incubated for 2 h at 37° C. and then washed 3 times with 300 µl of PBST (PBS 1, Tween 20: 0.05% (Merck 822184)). The reagent Aminolink 2 enables an arm containing a 6-aminohexyl group to be added at the 5' end of the probe. The probe coupled in this way to a ligand possessing a polar (primary amine) group, and bound passively to the support, elicits an improved signal; see Application FR 91/09057.

The target consisting of 10 µl of extract of total RNAs is mixed with 40 µl of PBS-salmon buffer (PBS 3+10 µg/ml salmon sperm DNA (Sigma D 9156)). The mixture is added into the well in which the capture probe is bound, with 50 µl of a solution of the oligonucleotide-peroxidase conjugate, constituting the detection probe, at an oligonucleotide concentration of 0.1 ng/µl in a PBS-horse buffer (PBS 3+10% horse serum (BioMé rieux 55842)). The plate is incubated for 1 h at 37° C. and then washed 3 times with 300 µl of PBST buffer. Into each well are added 100 µl of OPD (ortho-phenylenediamine, Cambridge Medical Biotechnology ref/456) substrate in a 0.055 M citric acid, 0.1 M sodium monohydrogen phosphate buffer, pH 4.93, at a concentration of 4 mg/ml, to which 30% hydrogen peroxide diluted to 1/1000 is added at the time of use. After 20 min of reaction, the enzyme activity is blocked with 100 µl of 1N sulfuric acid and reading is performed on an Axia Microreader (AXIA: registered trademark) apparatus (bioMé rieux) at 492 nm.

The target bacteria were, in particular, the following:
  8 isolates of *Corynebacterium striatum*
  1 strain of the following species:
    *Corynebacterium afermantans afermantans*
    *Corynebacterium afermantans lipophilum*
    *Corynebacterium amoniagenes* (nonpathogenic)
    *Corynebacterium amycolatum*
    *Corynebacterium argentoratense*
    *Corynebacterium asperum*
    *Corynebacterium bovis*
    *Corynebacterium callunae* (nonpathogenic)
    *Corynebacterium cystitidis*
    *Corynebacterium diphtheriae*
    *Corynebacterium flavescens*
    *Corynebacterium glutamicum* (nonpathogenic)
    *Corynebacterium jeikeium*
    *Corynebacterium matruchotii*
    *Corynebacterium minutissimum*
    *Corynebacterium mycetoides*
    *Corynebacterium pilosum*
    *Corynebacterium propinquum* (nonpathogenic)
    *Corynebacterium pseudodiphteriticum*
    *Corynebacterium pseudotuberculosis*
    *Corynebacterium seminale*
    Corynebacterium sp group F-1
    *Corynebacterium ulcerans*
    *Corynebacterium urealyticum*
  other bacterial species:
    *M. tuberculosis, N. asteroï des, R. equi*

The results obtained indicate that the combination of probes used is, a posteriori, specific for *Corynebacterium striatum*. It does not display a cross reaction with the nucleic acids, especially the ribosomal RNA, of the other bacterial species. It was checked that the target ribosomal RNAs of the other species are indeed released during the step of lysis, since they react with a combination of capture and detection probes directed against 16S ribosomal RNA and of eubacterial specificity.

Adaptation of the specific combination to the VIDAS (registered trademark—marketed by the company bioMé rieux-VITEK) automated system was performed. The wall of the microplate well is replaced here by the SPR (trademark) ("Solid Phase Receptacle"), which is a conical support made from a material sold under the name K resin (butadiene-styrene copolymer) and marketed by the company bioMé rieux-VITEK (U.S.A.). The various reagents are arranged in a multicuvette carrier bar, and the different steps proceed in the SPR which is capable of drawing in and expelling the reagents and which hence acts as a pipette. The sandwich hybridization reaction described in the protocol below takes place on the inner wall of the cone.

The capture oligonucleotide containing the ligand Aminolink 2 (Applied Biosystems ref. 400808) at its 5' end, at a concentration of 1 ng/µl in a volume of 315 µl of a PBS 4 solution (200 mM sodium phosphate, pH 7.0, 600 mM NaCl), is bound passively to the inner surface of the SPR. After one night at room temperature or two hours at 37° C., the cones are washed twice with a PBS-Tween solution and then dried under vacuum. The carrier bar contains in cuvettes the reagents needed for the detection, that is to say:

200 µl of a solution at a concentration of 0.1 ng/µl of the oligonucleotidealkaline phosphatase detection conjugate, twice 600 µl of PBS-Tween washing solution and a cuvette of substrate.

10 µl of the extracted RNA, in the same buffer as for the microplate protocol above, are introduced into the first well of the carrier bar.

After incubation of the cone for 30 minutes with the target plus detection probe mixture, the cone is washed twice with a PBS-Tween solution. 250 µl of MUP (4-methylumbelliferyl phosphate) substrate dissolved in a diethanolamine buffer are drawn into the cone and then released into a reading cuvette. The apparatus measures the fluorescence signal expressed in RFU (relative fluorescence units) of the cuvette.

The results obtained with this system are the same as those obtained in microplates.

We claim:

1. An isolated single stranded nucleic acid fragment of 16S ribosomal RNA of a pathogenic species of the genus Corynebacterium which consists of a nucleotide sequence selected from the group consisting of SEQ ID NO: 1 to SEQ ID NO: 91 and those sequences fully complementary thereto.

2. An isolated single stranded nucleic acid fragment of DNA obtained by reverse transcription of a nucleic acid fragment which fragment consists of a nucleotide sequence selected from the group consisting of SEQ ID NO: 1 to SEQ ID NO: 91 and those sequences fully complementary thereto.

3. A method for the selective detection and/or the identification of a pathogenic species of corynebacteria in a biological sample comprising:
   (a) exposing under hybridizing conditions at least one probe with 16S ribosomal RNA extracted from said biological sample wherein said at least one probe consists of a nucleotide sequence selected from the group consisting of:
      (i) an RNA sequence selected from the group consisting of SEQ ID NO: 1 to SEQ ID NO: 91 and those sequences fully complementary thereto,
      (ii) a DNA sequence corresponding to said RNA sequence, and
      (iii) a portion of said RNA or DNA sequence consisting of a succession of at least seven contiguous monomers of said RNA or DNA sequence; and
   (b) detecting the hybridization of said at least one probe with said ribosomal RNA wherein the detection of hybridization results in the selective detection and/or the identification of a pathogenic species of corynebacteria.

4. The method as claimed in claim 3, wherein said portion consists of a succession of at least eight contiguous monomers of said RNA or DNA sequence.

5. The method as claimed in claim 3, wherein said probe consists of said RNA or DNA sequence.

6. A method for the selective detection and/or the identification of a pathogenic species of corynebacteria in a biological sample comprising:
   (a) exposing under hybridizing conditions at least one probe with denatured bacterial genomic DNA extracted from said biological sample wherein said at least one probe consists of a nucleotide sequence selected from the group consisting of:
      (i) an RNA sequence selected from the group consisting of SEQ ID NO: 1 to SEQ ID NO: 91 and those sequences fully complementary thereto,
      (ii) a DNA sequence corresponding to said RNA sequence, and
      (iii) a portion of said RNA or DNA sequence consisting of a succession of at least seven contiguous monomers of said RNA or DNA sequence; and
   (b) detecting the hybridization of said at least one probe with said genomic DNA wherein the detection of hybridization results in the selective detection and/or the identification of a pathogenic species of corynebacteria.

7. The method as claimed in claim 6, wherein said portion consists of a succession of at least eight contiguous monomers of said RNA or DNA sequence.

8. The method as claimed in claim 6, wherein said probe consists of said RNA or DNA sequence.

9. The method as claimed in claim 6, wherein, before the genomic DNA is exposed to said probe, an amplification of said genomic DNA is carried out in the presence of an appropriate enzyme and at least one primer comprising a sequence of at least seven monomers which is identical or equivalent to at least a portion of a nucleotide sequence selected from the group consisting of SEQ ID NO: 1 to SEQ ID NO: 91, and their complementary sequences.

10. A method for the selective detection and/or the identification of a pathogenic species of corynebacteria in a biological sample comprising:
   (a) exposing under hybridizing conditions at least one probe with DNA obtained by the reverse transcription of 16S ribosomal RNA extracted from said biological sample wherein said at least one probe consists of a nucleotide sequence selected from the group consisting of:
      (i) an RNA sequence selected from the group consisting of SEQ ID NO: 1 to SEQ ID NO: 91 and those sequences fully complementary thereto,
      (ii) a DNA sequence corresponding to said RNA sequence, and
      (iii) a portion of said RNA or DNA sequence consisting of a succession of at least seven contiguous monomers of said RNA or DNA sequence; and
   (b) detecting the hybridization of said at least one probe with said DNA obtained by the reverse transcription wherein the detection of hybridization results in the selective detection and/or the identification of a pathogenic species of corynebacteria.

11. The method as claimed in claim 10, wherein said portion consists of a succession of at least eight contiguous monomers of said RNA or DNA sequence.

12. The method as claimed in claim 10, wherein said probe consists of said RNA or DNA sequence.

13. The method as claimed in claim 10, wherein, before the DNA is exposed to said probe, an amplification of said DNA is carried out in the presence of an appropriate enzyme and at least one primer comprising a sequence of at least seven monomers which is identical or equivalent to at least a portion of a nucleotide sequence selected from the group consisting of SEQ ID NO: 1 to SEQ ID NO: 91, and their complementary sequences.

14. A method for the selective detection and/or the identification of a pathogenic species of corynebacteria in a biological sample comprising:
   (a) exposing under hybridizing condition at least one probe with 16S ribosomal RNA extracted from said biological sample wherein said at least one probe comprises a succession of at least seven contiguous monomers of
      (i) an RNA sequence selected from the group consisting of SEQ ID NO: 1 to SEQ ID NO: 91, and those sequences fully complementary thereto, or
      (ii) a DNA sequence corresponding to said RNA sequence,
   wherein said at least one probe has no more than 30 monomers; and
   (b) detecting the hybridization of said at least one probe with said ribosomal RNA wherein the detection of hybridization results in the selective detection and/or the identification of a pathogenic species of corynebacteria.

15. The method as claimed in claim 14, wherein said probe comprises a succession of at least eight contiguous monomers of said RNA or DNA sequence.

16. The method as claimed in claim 14, wherein said probe comprises said RNA or DNA sequence.

17. A method for the selective detection and/or the identification of a pathogenic species of corynebacteria in a biological sample comprising:
   (a) exposing under hybridizing conditions at least one probe with denatured bacterial genomic DNA extracted from said biological sample wherein said at least one probe comprises a succession of at least seven contiguous monomers of
      (i) an RNA sequence selected from the group consisting of SEQ ID NO: 1 to SEQ ID NO: 91, and those sequences fully complementary thereto, or
      (ii) a DNA sequence corresponding to said RNA sequence,
   wherein said at least one probe has no more than 30 monomers; and
   (b) detecting the hybridization of said at least one probe with said genomic DNA wherein the detection of hybridization results in the selective detection and/or the identification of a pathogenic species of corynebacteria.

18. The method as claimed in claim 17, wherein said probe comprises a succession of at least eight contiguous monomers of said RNA or DNA sequence.

19. The method as claimed in claim 17, wherein said probe comprises said RNA or DNA sequence.

20. The method as claimed in claim 17, wherein, before the genomic DNA is exposed to said probe, an amplification of said genomic DNA is carried out in the presence of an appropriate enzyme and at least one primer comprising a sequence of at least seven monomers which is identical or equivalent to at least a portion of a nucleotide sequence selected from the group consisting of SEQ ID NO: 1 to SEQ ID NO: 91, and their complementary sequences.

21. A method for the selective detection and/or the identification of a pathogenic species of corynebacteria in a biological sample comprising:
   (a) exposing under hybridizing conditions at least one probe with DNA obtained by the reverse transcription of 16S ribosomal RNA extracted from said biological sample wherein said at least one probe comprises a succession of at least seven contiguous monomers of
      (i) an RNA sequence selected from the group consisting of SEQ ID NO: 1 to SEQ ID NO: 91, and those sequences fully complementary thereto, or
      (ii) a DNA sequence corresponding to said RNA sequence,
   wherein said probe has no more than 30 monomers; and
   (b) detecting the hybridization of said at least one probe with said DNA obtained by the reverse transcription wherein the detection of hybridization results in the selective detection and/or the identification of a pathogenic species of corynebacteria.

22. The method as claimed in claim 21, wherein said probe comprises a succession of at least eight contiguous monomers of said RNA or DNA sequence.

23. The method as claimed in claim 21, wherein said probe comprises said RNA or DNA sequence.

24. The method as claimed in claim 21, wherein, before the DNA is exposed to said probe, an amplification of said DNA is carried out in the presence of an appropriate enzyme and at least one primer comprising a sequence of at least seven monomers which is identical or equivalent to at least a portion of a nucleotide sequence selected from the group consisting of SEQ ID NO: 1 to SEQ ID NO: 91, and their complementary sequences.

* * * * *